Patented June 8, 1943

Plant Pat. 587

UNITED STATES PATENT OFFICE

587

NECTARINE

Signa Larsen Hayes, Fresno, Calif.

No Drawing. Application October 24, 1941,
Serial No. 416,361

1 Claim. (Cl. 47—62)

My invention relates to a plant invention or discovery, and more particularly to a new variety of nectarine. The special qualities of this variety which are new are a slightly different taste, having slightly more pronounced peach flavor, a different season for ripening in that it ripens several weeks later than those now being grown, a very firm flesh, which permit peeling of the fruit, and which gives it good shipping qualities, and which can be kept without rotting for a period longer than the same variety of fruit heretofore grown.

The following is a minute description of the species: The tree is of medium size, is vigorous, has spreading branches, with a round top, is dense, hardy, very productive and a regular bearer.

The trunk is medium stocky, and the bark is medium in smoothness.

The branches are medium stocky with a smooth exterior and a glossy brown in color.

The lenticels are few and small.

The leaves are approximately 5½ inches long and 1¼ inches wide, in shape are lanceolate with ovate tendencies, but are acutely pointed. The thickness of the leaves is medium, the color a medium green, i. e., between light green and dark green, the surface of the leaf is rugose, and the margin finely serrate. The petiole is long and medium in thickness. The glands are few, are alternate and medium in size. Said glands are globose, of a green color, and positioned at the base of the blade. They have no stipules.

The flower buds are hardy, large in size, short in length, are plump, appressed and pubescent. The flowers occur in California where the experiments have been had at the same time the peaches bloom, early in the spring, the flowers being medium in size and pink.

The fruit ripens late in the season, to-wit: about September 1. The keeping and shipping quality is excellent. In 1941 some of said nectarines were picked September 3rd and placed in cold storage on the same day, removed therefrom September 29, 1941, and kept until October 10th when they showed signs of deterioration, as they were subjected to the normal changes in temperature.

The fruit is large, the length being 2½ inches and largest diameter averaging 2½ inches, are regular in shape and roundish in shape. The halves of the fruit are approximately equal.

The cavity is medium in depth, medium in width, regular, and abrupt. The suture is medium and distinct. The apex is roundish. The color is a yellowish green with a red shaded splotch. The skin is medium in thickness, smooth, and adherent. The flesh is white in color, medium juicy and fine grained. The flesh is firm in texture, sweet and aromatic in taste. Quality is the very best.

The stone is large, ovate in shape and clinging to the flesh. It is conspicuously wing grooved, corrugated and pointed. The best use for it is to ship it to market because of its keeping and tasting qualities. Also good for canning.

The origin of the species is a seedling of a nectarine, the blossom of which was exposed to pollen from a late peach.

As compared with other well known varieties grown in the same general location in which my new variety has been developed, it is noted that the Quetta variety ripens early in August whereas my variety does not ripen until late August or early September, being a difference of approximately three to four weeks. The Stanwick, which is generally regarded as a late nectarine, ripens approximately a week earlier than my new variety, and the ripening time of the Victoria, which more nearly parallels the ripening time of my variety, ripens approximately a week before my improved nectarine. It should also be noted that the Stanwick and Victoria, the latest ripening varieties before my nectarine was developed, are freestone varieties, whereas my improved nectarine is of the clingstone variety. It is also noted that fruits of the clingstone variety are distinctive in taste from those of the freestone variety, and I claim for my new variety an aromatic and pleasing taste different from those of other varieties.

Having described my new variety of nectarines, I claim as new and ask for Letters Patent:

A new variety of nectarines as herein disclosed characterized by lateness of season for ripening, good shipping and good keeping qualities, having a sweet aromatic taste and firm clinging flesh.

SIGNA LARSEN HAYES.